United States Patent
Lee et al.

(10) Patent No.: US 12,029,615 B2
(45) Date of Patent: *Jul. 9, 2024

(54) ULTRASOUND DIAGNOSIS APPARATUS AND METHOD FOR GENERATING IMAGE FROM VOLUME DATA AND DISPLAYING THE SAME

(71) Applicant: SAMSUNG MEDISON CO., LTD., Gangwon-do (KR)

(72) Inventors: Kwang-hee Lee, Hongcheon-gun (KR); Sung-yoon Kim, Hongcheon-gun (KR); Jun-sang Yoo, Hongcheon-gun (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,936

(22) Filed: Apr. 19, 2022

(65) Prior Publication Data

US 2022/0233172 A1    Jul. 28, 2022

Related U.S. Application Data

(63) Continuation of application No. 16/566,360, filed on Sep. 10, 2019, now Pat. No. 11,324,486, which is a
(Continued)

(30) Foreign Application Priority Data

Aug. 5, 2014    (KR) .................. 10-2014-0100699

(51) Int. Cl.
*A61B 8/08*    (2006.01)
*A61B 5/00*    (2006.01)
(Continued)

(52) U.S. Cl.
CPC ............ *A61B 8/523* (2013.01); *A61B 5/7267* (2013.01); *A61B 8/0808* (2013.01);
(Continued)

(58) Field of Classification Search
CPC ..... A61B 8/0808; A61B 8/0866; A61B 8/463; A61B 8/5223; A61B 8/523;
(Continued)

(56) References Cited

U.S. PATENT DOCUMENTS 5,588,435 A    12/1996 Weng et al.
5,605,155 A    2/1997 Chalana et al.
(Continued)

FOREIGN PATENT DOCUMENTS

JP    2006-167100 A    6/2006
JP    2007-512862 A    5/2007
(Continued)

OTHER PUBLICATIONS

Communication dated May 25, 2021, issued by Korean Intellectual Property Office in Korean Patent Application No. 10-2014-0100699.
(Continued)

*Primary Examiner* — Amelie R Davis
(74) *Attorney, Agent, or Firm* — Morgan, Lewis & Bockius LLP

(57) ABSTRACT

The ultrasound diagnosis apparatus includes a display configured to display a mid-sagittal plane (MSP) image corresponding to the MSP of a head of an object, and an image processor configured to determine a measurement plane based on the MSP and generate a measurement plane image corresponding to the measurement plane. The display is further configured to display the measurement plane image with the MSP image.

20 Claims, 9 Drawing Sheets

Related U.S. Application Data continuation of application No. 14/818,470, filed on Aug. 5, 2015, now Pat. No. 10,433,819.

(51) Int. Cl.
  *A61B 8/00* (2006.01)
  *G06T 7/62* (2017.01)
(52) U.S. Cl.
  CPC .............. *A61B 8/0866* (2013.01); *G06T 7/62* (2017.01); *A61B 8/463* (2013.01); *A61B 8/468* (2013.01); *A61B 8/483* (2013.01); *A61B 8/5207* (2013.01); *A61B 8/5223* (2013.01); *G06T 2207/10136* (2013.01); *G06T 2207/30016* (2013.01); *G06T 2207/30044* (2013.01)
(58) Field of Classification Search
  CPC . G06T 2207/10136; G06T 2207/30016; G06T 2207/30044; G06T 7/62
  See application file for complete search history.

(56) References Cited

U.S. PATENT DOCUMENTS

| | | | |
|---|---|---|---|
| 6,019,723 | A | 2/2000 | Yamaura |
| 6,939,301 | B2 | 9/2005 | Abdelhak |
| 7,925,064 | B2 | 4/2011 | Cloutier et al. |
| 7,985,182 | B2 | 7/2011 | Ichioka et al. |
| 8,083,678 | B2 | 12/2011 | Abuhamad |
| 8,556,814 | B2 | 10/2013 | Monteiro de Barros Carneiro et al. |
| 8,915,855 | B2 | 12/2014 | Lee |
| 2002/0103429 | A1 | 8/2002 | deCharms |
| 2005/0187472 | A1 | 8/2005 | Lysyansky et al. |
| 2005/0228250 | A1 | 10/2005 | Bitter et al. |
| 2005/0283078 | A1 | 12/2005 | Steen |
| 2007/0249935 | A1 | 10/2007 | Deschinger et al. |
| 2008/0167581 | A1 | 7/2008 | Paltieli |
| 2009/0093716 | A1 | 4/2009 | Deischinger et al. |
| 2009/0093717 | A1 | 4/2009 | Carneiro et al. |
| 2010/0217123 | A1 | 8/2010 | Eran et al. |
| 2010/0232405 | A1 | 9/2010 | Kikuchi |
| 2011/0028842 | A1 | 2/2011 | Lee et al. |
| 2011/0054324 | A1 | 3/2011 | Lee |
| 2011/0172536 | A1 | 7/2011 | Do et al. |
| 2011/0224546 | A1 | 9/2011 | Lee et al. |
| 2011/0282202 | A1 | 11/2011 | Lee et al. |
| 2012/0065512 | A1 | 3/2012 | Hamada et al. |
| 2012/0157841 | A1 | 6/2012 | Glaenzer et al. |
| 2013/0072797 | A1 | 3/2013 | Lee |
| 2013/0218015 | A1 | 8/2013 | Machtey et al. |

FOREIGN PATENT DOCUMENTS

| | | |
|---|---|---|
| KR | 10-2012-0028154 A | 3/2012 |
| KR | 10-1121379 B1 | 3/2012 |

OTHER PUBLICATIONS

U.S. Non-Final Office Action dated Nov. 20, 2020 issued in U.S. Appl. No. 16/566,360.
U.S. Final Office Action dated Apr. 30, 2021 issued in U.S. Appl. No. 16/566,360.
U.S. Non-Final Office Action dated Jul. 7, 2021 issued in U.S. Appl. No. 16/566,360.
Notice of Allowance dated Jan. 14, 2022 issued in U.S. Appl. No. 16/566,360.
Cameiro, Gustavo & Amat, Fernando & Georgescu, Bogdan & Good, S & Comaniciu, Dorin, (2008), Semantic-based indexing of fetal anatomies from 3-D ultrasound data using global/semi-local context and sequential sampling, Proc. IEEE Conf. Computer Vision and Pattern Recognition, 1-8 (Year 2008).
The International Society of Ultrasound in Obstetrics & Gynecology (ISUOG), "Sonographic examination of the fetal central nervous system: guidelines for performing the "basic examination" and the 'fetal neurosonogram'," Ultrasound Obstet Gynecol, 29: (2007), pp. 109-116, doi: 10.1002/uog.3909 XP055040876.
Kwang Hee Lee et al., "Robust Mid-Sagittal Plane Extraction in 3-D Ultrasound Fetal vol. for First Trimester Screening," ACCV 2012, Part II, LNCS 7725, pp. 316-329, 2013.
Communication dated Dec. 15, 2015, from the European Patent Office in counterpart European Patent Application No. 15176103.8.

ULTRASOUND DIAGNOSIS APPARATUS AND METHOD FOR GENERATING IMAGE FROM VOLUME DATA AND DISPLAYING THE SAME

CROSS-REFERENCE TO RELATED APPLICATIONS

This is a continuation of U.S. application Ser. No. 16/566,360 filed Sep. 10, 2019, which is a continuation of U.S. application Ser. No. 14/818,470 filed Aug. 5, 2015, which claims priority from Korean Patent Application No. 10-2014-0100699, filed Aug. 5, 2014, in the Korean Intellectual Property Office. The disclosures of the above-named applications are incorporated herein by reference in their entireties.

BACKGROUND

1. Field

One or more exemplary embodiments relate to an ultrasound diagnosis apparatus, and more particularly, to an ultrasound diagnosis apparatus for measuring a fetal head based on a three-dimensional (3D) ultrasound image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to no radiation exposure, compared to X-ray apparatuses. Therefore, an ultrasound diagnosis apparatus is widely used together with other types of imaging diagnosis devices.

In prenatal ultrasound, an ultrasound diagnosis apparatus produces an ultrasound image of a fetus by transmitting ultrasound signals to an object and receiving ultrasound echo signals reflected from the object. In addition, the ultrasound diagnosis apparatus may diagnose a disease in the fetus by measuring the head size of the fetus, and in particular, head circumference (HC), biparietal diameter (BPD), and occipitofrontal diameter (OFD).

Conventionally, to measure a fetus's head size, a two-dimensional (2D) ultrasound image of a cross-sectional plane from which biometric parameters for a fetal head such as HC and BPD are to be measured are obtained by performing a plurality of scans of the fetus. Thus, according to the conventional measuring method, an ultrasound scan needs to be repeated until an ultrasound image of a desired cross-sectional plane is acquired, and thus, it takes a long time to measure a the size of the head of a fetus. Furthermore, since the accuracy of a cross-sectional plane to be acquired may vary depending on the skill level of a medical practitioner who performs an ultrasound scan, it is difficult to accurately measure fetal HC, OFD, and BPD.

SUMMARY

One or more exemplary embodiments include an ultrasound diagnosis apparatus configured to automatically acquire a measurement plane where biometric parameters are to be measured.

One or more exemplary embodiments include an ultrasound diagnosis apparatus configured to allow a user to easily and quickly measure biometric parameters.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a data acquisition unit configured to acquire volume data for a head of an object; an image processor configured to detect a mid-sagittal plane (MSP) from the volume data, generate an MSP image corresponding to the MSP, detect at least one measurement plane based on the MSP, and generate at least one measurement plane image corresponding to the at least one measurement plane; and a display configured to display the MSP image and the at least one measurement plane image on a single screen.

The image processor may acquire a measured value by measuring at least one biometric parameter in the at least one measurement plane image and indicate the measured value on at least one of the at least one measurement plane image and the MSP image.

The position of the at least one measurement plane may be indicated by at least one line on the MSP image.

The at least one line may be indicated in different colors.

The image processor may indicate the measured value on at least one of the at least one measurement plane image and the MSP image by using at least one of a marker and a text.

The display may display on the single screen at least one selected from the measured value, a position of the at least one biometric parameter, a statistical value of a fetal gestational age (number of weeks of pregnancy), and a statistical graph.

The display may display the MSP image and the at least one measurement plane image in a 2×2 layout.

The display may display the MSP image and the at least one measurement plane image in a 2×1 layout.

The image processor may indicate a contour of the at least one measurement plane image in the same color as a line corresponding to the at least one measurement plane indicated on the MSP image.

The image processor may indicate a name of the at least one measurement plane on the at least one measurement plane image in the same color as a line corresponding to the at least one measurement plane indicated on the MSP image.

The at least one biometric parameter may include head circumference (HC), biparietal diameter (BPD), occipital frontal diameter (OFD), transverse cerebellar diameter (TCD), cisterna magna (CM), and posterior ventricle (Vp).

The image processor may extract a falx from the volume data based on user input information and detects the MSP by using the falx or automatically detect the MSP by using a machine learning technique.

The at least one measurement plane may include at least one selected from a transthalamic plane (TTP), a transventricular plane (TVP), or a transcerebella plane (TCP).

The image processor may determine one of a plurality of candidate planes that are perpendicular to the MSP as the TTP, based on a brightness value of a predetermined region.

The image processor may determine one of a plurality of candidate planes that are perpendicular to the MSP and horizontal to the TTP as the TVP, based on a gradient magnitude of a predetermined region.

The image processor may detect a cavum septi pellucidi (CSP) that is a predetermined distance from a central point of the head towards an anterior part of the head in the TTP and determine, as the TCP, one of a plurality of candidate planes obtained by rotating the 11P around the CSP as a central axis, based on similarity of a predetermined pattern in a predetermined region.

The image processor may measure the at least one biometric parameter by using at least one of an image processing technique and a machine learning classifier.

The ultrasound diagnosis apparatus may further include a user interface configured to receive a request to change a measurement plane.

The image processor may change at least one of a measurement plane image and the at least one line in response to the request and changes a measured value based on the changed measurement plane image.

The user interface may output a menu via which at least one of rotation, movement, and scaling of the at least one line is performed.

When the image processor receives a request to change the at least one measurement plane, the image processor may change the measured value by remeasuring the at least one biometric parameter in response to the request.

When the image processor receives information of selection of a line from among at least one line on the MSP image from the user, the image processor may highlight the measurement plane image corresponding to the selected line.

When the image processor receives information of selection of one measurement plane image from among the at least one measurement plane image from the user, the image processor may highlight a line among the at least one line corresponding to the measurement plane.

According to the one or more exemplary embodiments, the ultrasound diagnosis apparatus enables quicker and easier diagnosis of abnormality of a fetal brain based on three-dimensional (3D) volume data. Furthermore, the ultrasound diagnosis apparatus allows the user to select a desired measurement plane and identify a position of biometric parameters. In addition, inter-observer variance and intra-observer variance in the measurement of an object may be reduced.

BRIEF DESCRIPTION OF THE DRAWINGS

The above and other features and advantages of the present invention will become more apparent by describing in detail exemplary embodiments thereof with reference to accompanying drawings in which.

DETAILED DESCRIPTION

Figure 1:
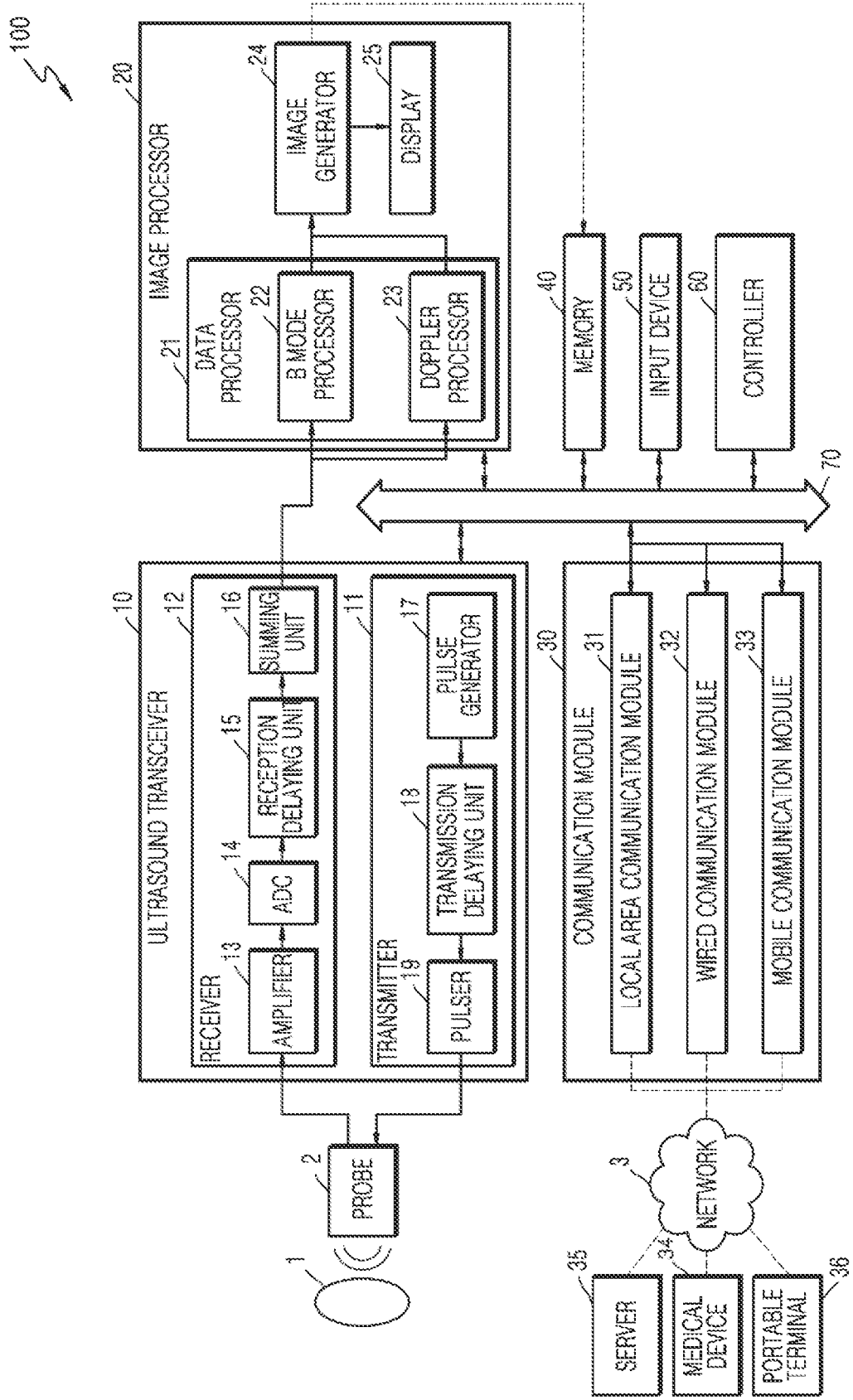
FIG. 1 is a block diagram of an ultrasound diagnosis apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the invention. Thus, the terms used herein should be defined not as simple names thereof but based on their meaning and the overall description of the inventive concept.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

FIG. 1 illustrates an overall configuration of an ultrasound diagnosis apparatus 100 according to an exemplary embodiment.

Referring to FIG. 1, the ultrasound diagnosis apparatus 100 may include a probe 2, an ultrasound transceiver 10, an image processor 20, a communication module 30, a memory 40, an input device 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly, and according to embodiments, the ultrasound diagnosis apparatus 100 may include a plurality of probes 2.

A transmitter 11 supplies a driving signal to the probe 2. The transmitter 110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components 22.

Similarly, a Doppler processor 23 may extract Doppler components from ultrasound data, and the image generator 24 may generate a Doppler image indicating a movement of an object as colors or waveforms based on the extracted Doppler components.

According to an embodiment, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 300 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 300 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The input device 50 refers to a means via which a user inputs data for controlling the ultrasound diagnosis apparatus 100. The input device 50 may include hardware components, such as a keypad, a mouse, a touch panel, a touch screen, and a jog switch. However, embodiments are not limited thereto, and the input device 50 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the input device 50 shown in FIG. 1.

All or some of the probe 2, the ultrasound transceiver 10, the image processor 20, the communication module 30, the memory 40, the input device 50, and the controller 60 may be implemented as software modules. However, embodiments of the present invention are not limited thereto, and some of the components stated above may be implemented as hardware modules. Furthermore, at least one selected from the ultrasound transceiver 10, the image processor 20, and the communication module 30 may be included in the controller 60. However, embodiments of the present invention are not limited thereto.

For diagnosis of disease using an ultrasound image, a marker may be set for setting a target region in an ultrasound image including an object or for indicating a predetermined position therein.

In detail, the marker may be set at a region that is to be observed in detail by the user to diagnose a disease or to check the health status of a patient. The present invention provides an ultrasound diagnosis apparatus and a method of displaying an ultrasound image, which are capable of changing and outputting an ultrasound image to more accurately diagnose a region of an object where the marker is set.

Figure 2:
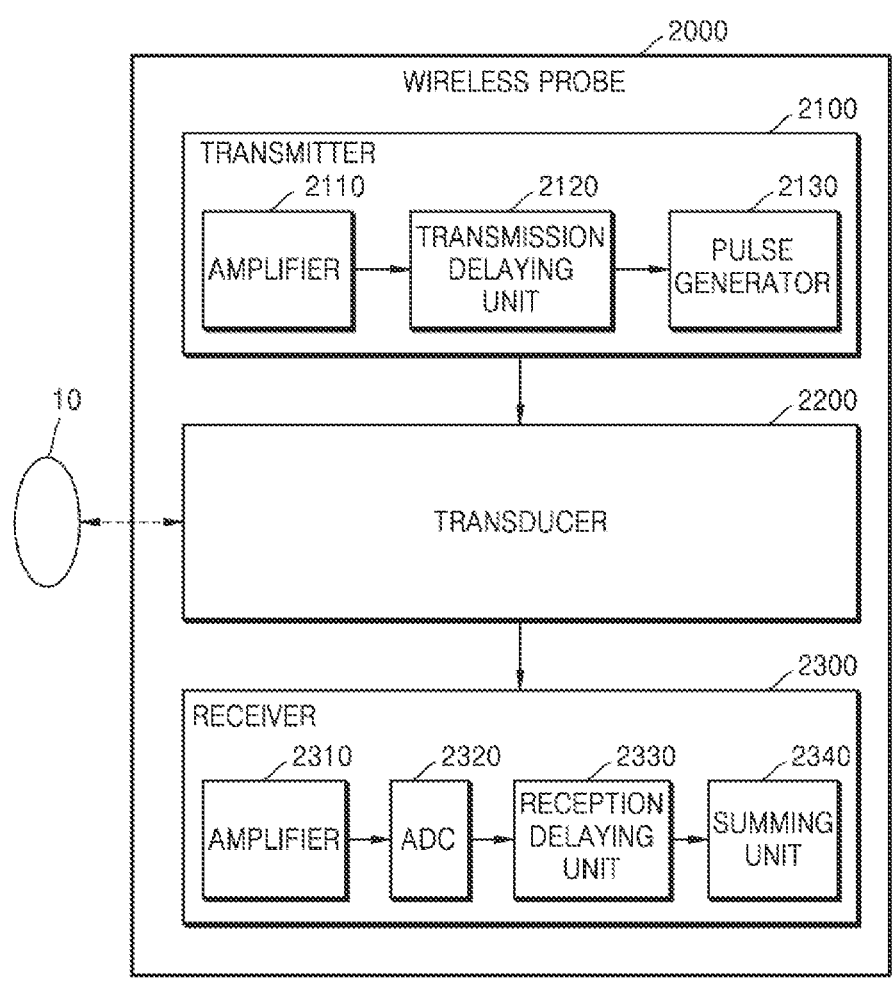
FIG. 2 is a block diagram of a wireless probe according to an exemplary embodiment.

FIG. 2 is a block diagram showing a configuration of a wireless probe 2000 according to an embodiment of the present invention. As described above with reference to FIG. 1, the wireless probe 2000 may include a plurality of transducers, and, according to embodiments of the present invention, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments of the present invention, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

The ultrasound diagnosis apparatus 100 may acquire an ultrasound image and measure various biometric parameters which can be used to determine a state of an object based on the acquired ultrasound image. Biometric parameters will now be described in detail with reference to FIG. 3.

Figure 3:
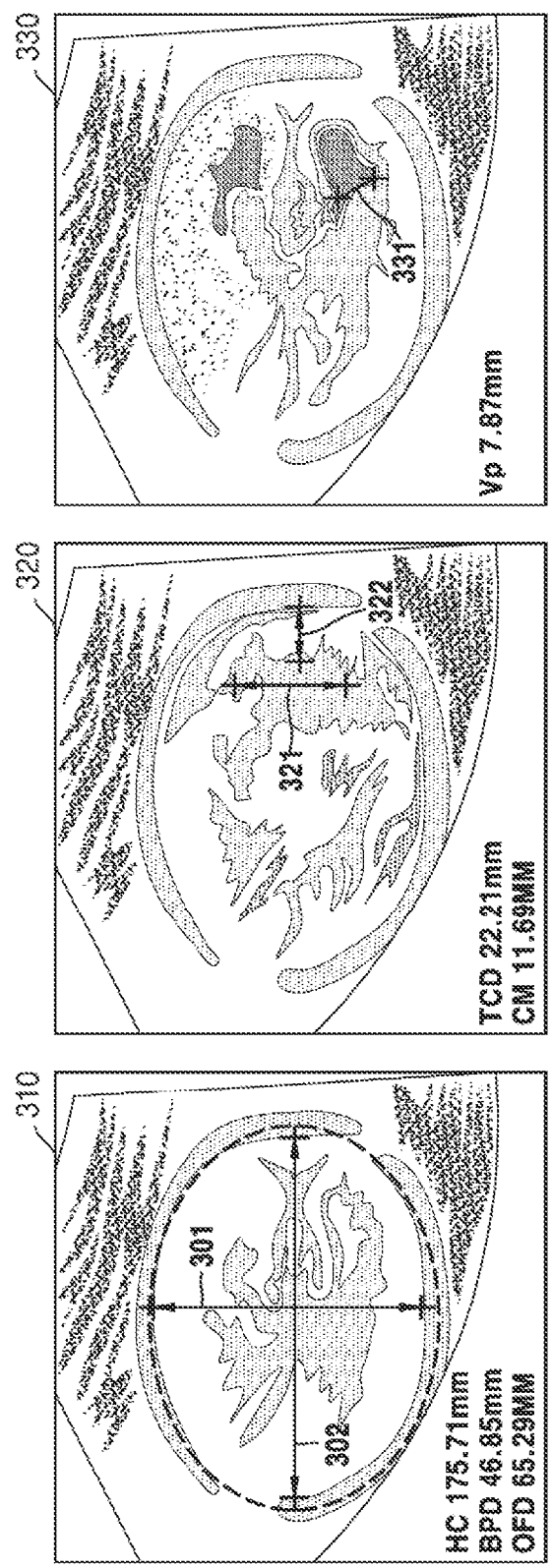
FIG. 3 is a conceptual diagram illustrating biometric parameters.

FIG. 3 is a conceptual diagram illustrating biometric parameters.

It is hereinafter assumed that an object is a fetus. If the object is fetus, biometric parameters may include head circumference (HC), biparietal diameter (BPD), Occipital frontal diameter (OFD), transverse cerebellar diameter (TCD), cisterna magna (CM), and posterior ventricle (Vp).

A transthalamic plane (TTP), a transventricular plane (TVP), a transcerebellar plane (TCP), etc. may be used as standard planes for measuring biometric parameters.

FIG. 3 illustrates a TTP 310, a TCP 320, and a TVP 330. Predefined measurement planes are needed to measure biometric parameters corresponding to the TTP 310, the TCP 320, and the TVP 330, respectively.

In detail, the TTP 310 is used for measurement of HC (indicated by a dashed line around the circumference of a head), BPD 301, and OFD 302. The TCP 320 is needed for measurement of TCD 321 and CM 322, and the TVP 330 enables measurement of Vp 331.

Selection of measurement planes is a critical task for accurate measurement of biometric parameters. In a conventional measuring method, since each measurement is performed on a new plane, ranges of inter-observer variance and intra-observer variance in the measurement of an object are wide. This results in a large error range in acquiring a measurement plane, thus making it difficult to acquire an accurate measurement plane.

To solve these problems, an ultrasound diagnosis apparatus according to an exemplary embodiment is configured to automatically acquire a measurement plane and display the measurement plane on a screen together with various pieces of information (e.g., position information of the measurement plane, measured values of biometric parameters, etc.) as described below. This configuration may facilitate review and modification and increase accuracy in acquiring a measurement plane by minimizing ranges of inter-observer variance and intra-observer variance. The operation of the ultrasound diagnosis apparatus according to an exemplary embodiment will now be described in more detail with reference to FIGS. 4 and 5.

Figure 4:
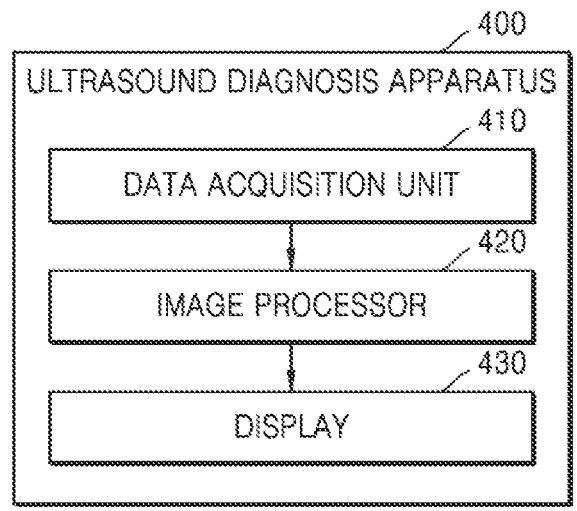
FIG. 4 is a block diagram of an ultrasound diagnosis apparatus according to an exemplary embodiment.

FIG. 4 is a block diagram of an ultrasound diagnosis apparatus 400 according to an exemplary embodiment.

The ultrasound diagnosis apparatus 400 according to the present exemplary embodiment may be included in the ultrasound diagnosis apparatus 100 described with reference to FIG. 1. In detail, a data acquisition unit 410, a controller 420, and a display 430 may correspond respectively to a data processor 21, the image generator 24, and the display 25 shown in FIG. 1.

Furthermore, the ultrasound diagnosis apparatus 400 may correspond to the medical apparatus 34 or the portable terminal 36 and may receive ultrasound data acquired by the ultrasound diagnosis apparatus 100 via a network 3 for use.

Referring to FIG. 4, the ultrasound diagnosis apparatus 400 may include the acquisition unit 410, the image processor 420, and the display 430.

The data acquisition unit 410 acquires volume data for a head of an object. In this case, the volume data may be 3D volume data of the object generated using ultrasound signals received via the probe. Furthermore, a 3D ultrasound image of the object may be generated using 3D volume data. A user may designate an ultrasound scanning range so as to include all biometric parameters.

The data acquisition unit 410 may acquire an axial plane of a fetal head as an initial plane and 3D volume data based on the acquired axial plane of the fetal head. In detail, the user may first designate an initial plane via the probe. In this case, the axial plane of the fetal head geometrically approximates at least one of a TTP, a TCP, and a TVP and may be arbitrarily selected by the user.

Then, the ultrasound diagnosis apparatus 400 may perform a two-dimensional (2D) scan on the designated initial plane for visualization. The user may check the fetal head in the initial plane via a screen and input a center of the fetal head and a direction of a fetal face, and in particular, an anterior direction thereof in the initial plane as a user input.

When the user inputs a scan command, a 3D ultrasound scan apparatus may perform a 3D ultrasound scan on the fetal head based on a user input and an initial plane, according to the user's scan command Through the above process, the data acquisition unit 410 may acquire 3D volume data for the fetal head.

The image processor 420 detects a mid-sagittal plane (MSP) from volume data to generate an MSP image corresponding to the MSP and then detects at least one measurement plane based on the MSP to generate at least one measurement plane image corresponding to the at least one measurement plane.

In detail, the image processor 420 may detect an MSP by extracting a falx cerebri from volume data based on the user input information. Furthermore, the image processor 420 may detect an MSP automatically by using symmetry information acquired from the volume data of an object.

In this case, a measurement plane is a plane in an object used that enables measurement of biometric parameters and may include a TTP, a TVP, a TCP, etc.

In other words, the image processor 420 may detect an MSP and then a TTP, a TVP, and a TCP based on the MSP. A method of detecting these measurement planes will be described in more detail below with reference to FIG. 6.

Furthermore, a user input may be a name of a plane that is to be detected. If the user enters a name of a desired plane, the ultrasound diagnosis apparatus 400 may display the desired plane on the screen as a measurement plane image. For example, if the user enters a TTP and a MSP, the ultrasound diagnosis apparatus 400 may display MSP and TTP images via a screen having a 2×1 layout.

Furthermore, the image processor 420 may indicate a position of at least one measurement plane on an MSP image. For example, the position of the at least one measurement plane may be indicated by a line or color. The line or color may accurately indicate which position of an MSP corresponds to the at least one measurement plane.

In this case, if a plurality of lines exists, the plurality of lines may be indicated in different colors. Furthermore, each of the plurality of lines may be indicated in the same color as a contour of its corresponding measurement plane image.

Furthermore, the image processor 420 may display a name of a measurement plane indicated on a measurement plane image in the same color as a line corresponding to the measurement plane on an MSP image.

The image processor 420 may also obtain a measured value by measuring a biometric parameter in at least one measurement plane image and display the measured value in at least one measurement plane image and an MSP image, as described in more detail below with reference to FIGS. 7 through 9.

In this case, the image processor 420 may measure a biometric parameter by using at least one of an image processing technique and a machine learning classifier. Since various techniques for measuring biometric parameters in a measurement plane are well known in the art, detailed descriptions thereof are omitted. In this case, machine learning is a field of artificial intelligence including algorithms that enable a computer to learn from a large amount of data. For example, machine learning algorithms may teach a computer to automatically find biometric parameters by using a large number of images with biometric parameters indicated thereon and automatically detect the biometric parameters via the taught computer to measure the biometric parameters.

Furthermore, the image processor 420 may indicate a measured value on at least one of a measurement plane image and an MSP image by using at least one of a marker and a text. For example, the image processor 420 may indicate a position of a biometric parameter on a measurement plane image by using a marker and a measured value on or near a measurement plane image as a text. In this case, the image processor 420 may indicate a marker and a text corresponding to one biometric parameter in a different color than that in which a marker and a text corresponding to another biometric parameter are indicated in order to distinguish the biometric parameters from each other.

Furthermore, the image processor 420 may extract a falx from volume data by using user input information and detect an MSP by using the flax. Alternatively, the image processor 420 may automatically detect an MSP by using a machine learning technique. Since various techniques for automatically detecting an MSP are well known in the art, detailed descriptions thereof are omitted.

The display 430 may display an MSP image and at least one measurement plane image on a single screen. For example, the display 430 may display a plurality of ultrasound images in various layouts. In detail, the display 430 may display MSP, TTP, TVP, and TCP images in a 2×2 layout on a single screen. Alternatively, the display 430 may display an MSP image and one of TTP, TVP, and TCP images in a 2×1 or 1×2 layout on a single screen.

Furthermore, the display 430 may display at least one of a measured value, a position of a biometric parameter, a statistical value of the gestational age of a fetus (number of weeks of pregnancy)), and a statistical graph on a single screen.

Furthermore, the display 430 may combine at least one of a user input, position information of an initial plane, a result of searching for a measurement plane, a result of detection of a landmark, and a result of automatic measurement to thereby display a position (e.g., Anterior, Posterior, Inferior, Superior, Left (Lt), and Right (Rt)) of at least one anatomical landmark (e.g., Cavum Septi Pellucidi (CSP), Cerebellum, Vp, Thalami, Choroid Plexus, and Lateral Ventricle) on a screen.

Figure 5:
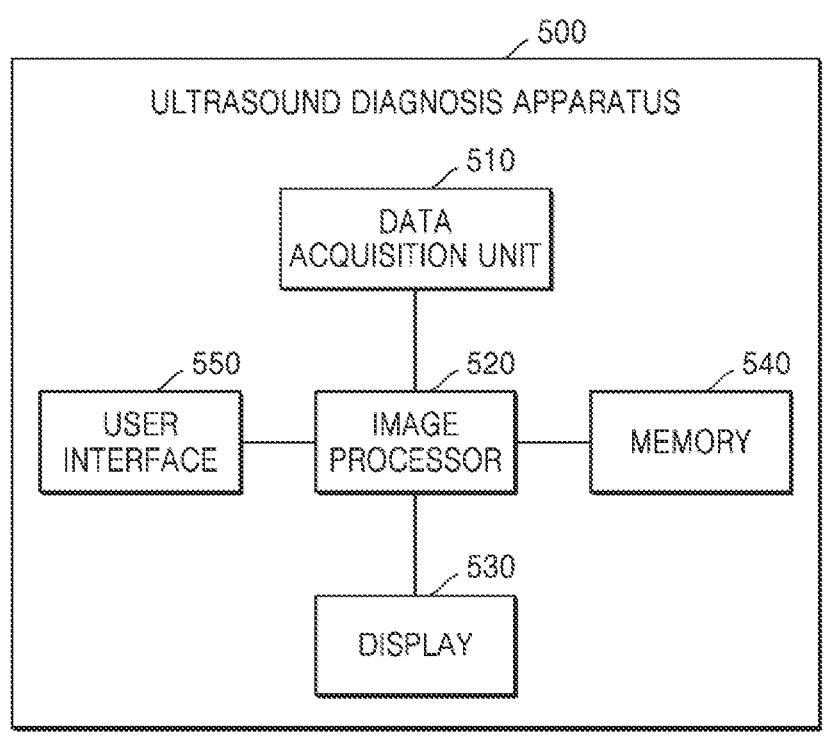
FIG. 5 is a block diagram of an ultrasound diagnosis apparatus according to an exemplary embodiment.

FIG. 5 is a block diagram of an ultrasound diagnosis apparatus 500 according to an exemplary embodiment.

A data acquisition unit 510, an image processor 520, and a display 530 operate in the same way as described with reference to FIG. 4.

A memory 540 stores various data processed by the ultrasound diagnosis apparatus 500. For example, the memory 540 may store medical data related to diagnosis of an object, such as ultrasound data and an ultrasound image that are input or output, and may also store algorithms or programs which are to be executed in the ultrasound diagnosis apparatus 500.

The memory 540 may be any of various storage media, e.g., a flash memory, a hard disk drive, EEPROM, etc. Furthermore, the ultrasound diagnosis apparatus 500 may utilize web storage or a cloud server that performs the storage function of the memory 540 online.

A user interface 550 may receive a request to change a measurement plane from a user. Furthermore, the user interface 550 may receive a request to change a measured value from the user.

According to an exemplary embodiment, the user interface 550 may output a menu via which at least one of rotation, movement, and scaling of a line on an MSP image is performed. In other words, the user may change a measurement plane by rotating, moving, or scaling a line corresponding to the measurement plane on the MSP image via the user interface 550.

The user interface 550 may also output a menu via which at least one of rotation, movement, and scaling of a volume in an MSP image is performed. In other words, the user may change a measurement plane by rotating, moving, and scaling a volume corresponding to the MSP image.

For example, if the user checks a measurement plane via the display 530 to determine that the measurement plane or a measured value is wrong, the user may change the measurement plane or measured value by controlling a line corresponding to the measurement plane on an MSP image or changing a geometry of a brain volume by ultrasound.

The ultrasound diagnosis apparatus 500 according to exemplary embodiments may provide a manual measurement function via the user interface 530.

Once the ultrasound diagnosis apparatus 500 receives information of selection of a line from among at least one line on an MSP image from the user, the ultrasound diagnosis apparatus 500 may highlight a measurement plane image corresponding to the selected line. For example, if the user selects a line corresponding to a TTP from among lines which are indicated on the MSP image and correspond to the TTP, TCP, and TVP, the ultrasound diagnosis apparatus 500 may highlight a TTP image for the user to recognize the TTP image e.g., by changing a color, a saturation, and a brightness of the TTP image or changing a thickness of a line thereof.

Furthermore, once the ultrasound diagnosis apparatus 500 receives information of selection of a measurement plane image from among at least one measurement plane image from the user, the ultrasound diagnosis apparatus 500 may highlight a line among at least one line corresponding to the measurement plane. For example, if MSP, TTP, TVP, and TCP images are displayed in a 2×2 layout, and the user selects the TTP image, the ultrasound diagnosis apparatus 500 may highlight a line corresponding to the TTP on the MSP image in order for the user to recognize the line, e.g., by changing a color, a saturation, a brightness, and a thickness of the line.

According to exemplary embodiments, the image processor 520 may change a measured value by remeasuring a biometric parameter in response to a user request to change the measured value. For example, if the user interface 530 outputs a menu via which a request to change a measured value is performed, the user may select the request.

According to exemplary embodiments, the image processor 520 may change a measurement plane image and at least one line among at least one line corresponding to the measurement plane displayed on a screen in response to a request to change a measurement plane, and a measured value based on the changed measurement plane image.

Figure 6:
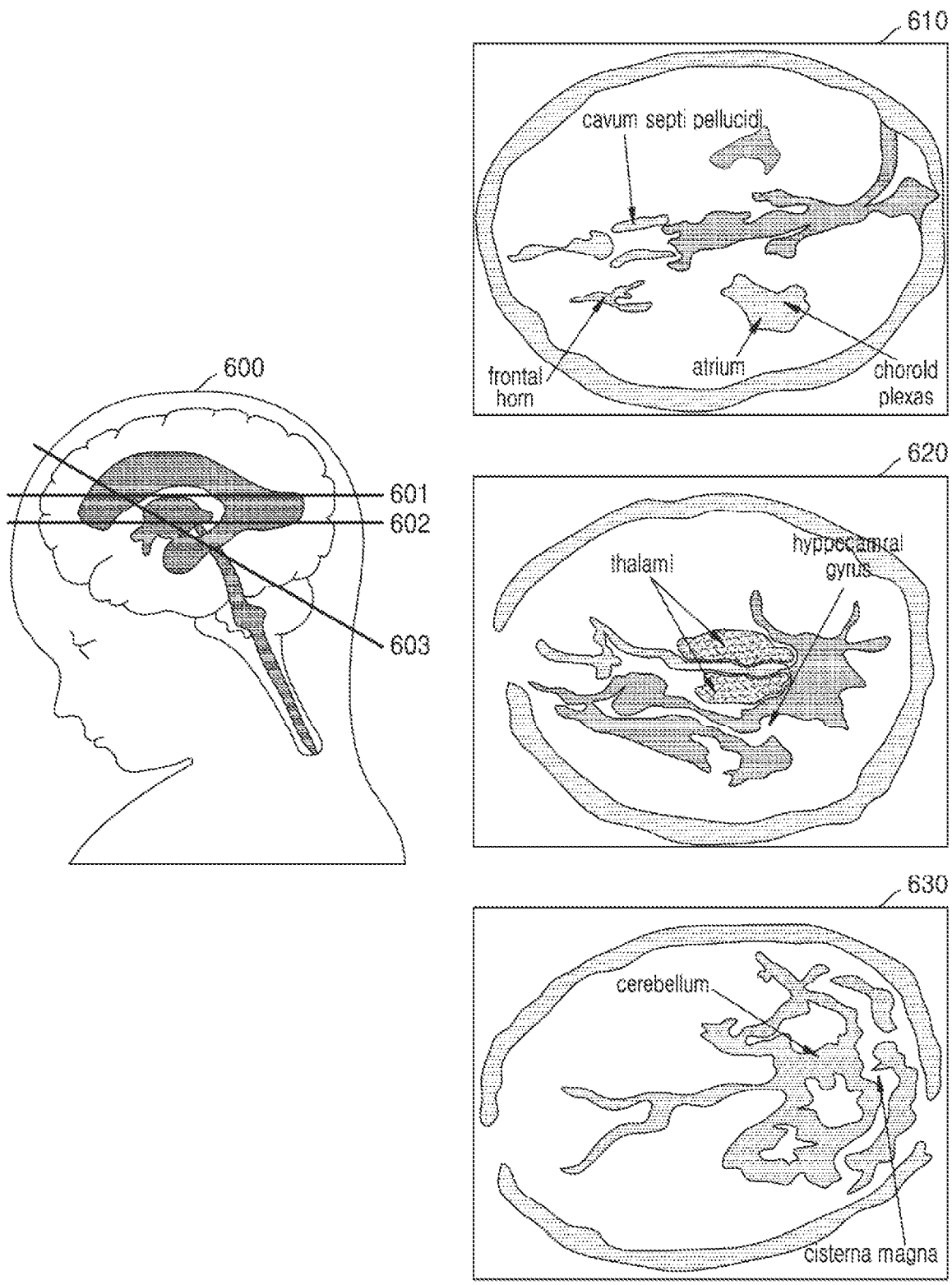
FIG. 6 is a conceptual diagram illustrating measurement planes.

FIG. 6 is a conceptual diagram illustrating measurement planes.

As described above, the image processor 520 detects an MSP from volume data and at least one measurement plane based on the detected MSP. FIG. 6 is a detailed diagram of the MSP and the at least one measurement plane detected by the image processor 520.

In detail, FIG. 6 illustrates axial views of a fetal head, from among which measurement planes are to be selected. 610, 620, and 630 respectively denote TVP, TTP, and TCP. A plurality of lines 601 through 603 are indicated in a fetal head image 600 and respectively correspond to the TVP 610, the TTP 620, and the TCP 630. According to exemplary embodiments, measurement planes may be detected based on an MSP. Detection of the MSP will now be described.

In detail, the image processor 520 may detect a falx from 3D ultrasound volume data by using user input information. In this case, the user input information may be a center of a fetal head and a direction of a fetal face. According to exemplary embodiments, the image processor 520 may detect an MSP by using the falx. Alternatively, the image processor 520 may automatically detect an MSP by using a machine learning technique.

According to exemplary embodiments, a method of determining measurement planes based on a detected MSP will now be described.

The image processor 520 may select a plane having a highest or lowest score as each of measurement planes, from among a plurality of candidate planes that are perpendicular to an MSP. In this case, a score may represent similarity between each of the candidate planes and a measurement plane. For example, the score may be determined by a machine learning classifier, or may be a brightness value of a specific region or the total sum of gradient magnitudes.

For example, the image processor 520 may determine one of a plurality of candidate planes that are perpendicular to an MSP as the TTP 620 based on a brightness value of a predetermined region. In this case, the predetermined region may be an arbitrary region at the rear part of a fetal head. In other words, the image processor 520 may measure a brightness value of a posterior region of a fetal head to determine a plane having a largest brightness value as the TTP 620.

Furthermore, the image processor 520 may detect a CSP that is located in a predetermined distance from a central point of a fetal head towards an anterior part thereof in the TTP 620 and determine as the TCP 630 one of a plurality of candidate planes obtained by rotating the TTP 620 around the CSP as a central axis, based on similarity of a predetermined pattern in a predetermined region. The predetermined region may be an arbitrary region including CSP, TCD, and CM.

The image processor 520 may also determine one of a plurality of candidate planes that are perpendicular to the MSP and horizontal to the TTP 620 as the TVP 610, based on a gradient magnitude of a predetermined region. In this case, the predetermined region may be an arbitrary region including Vp.

Figure 7:
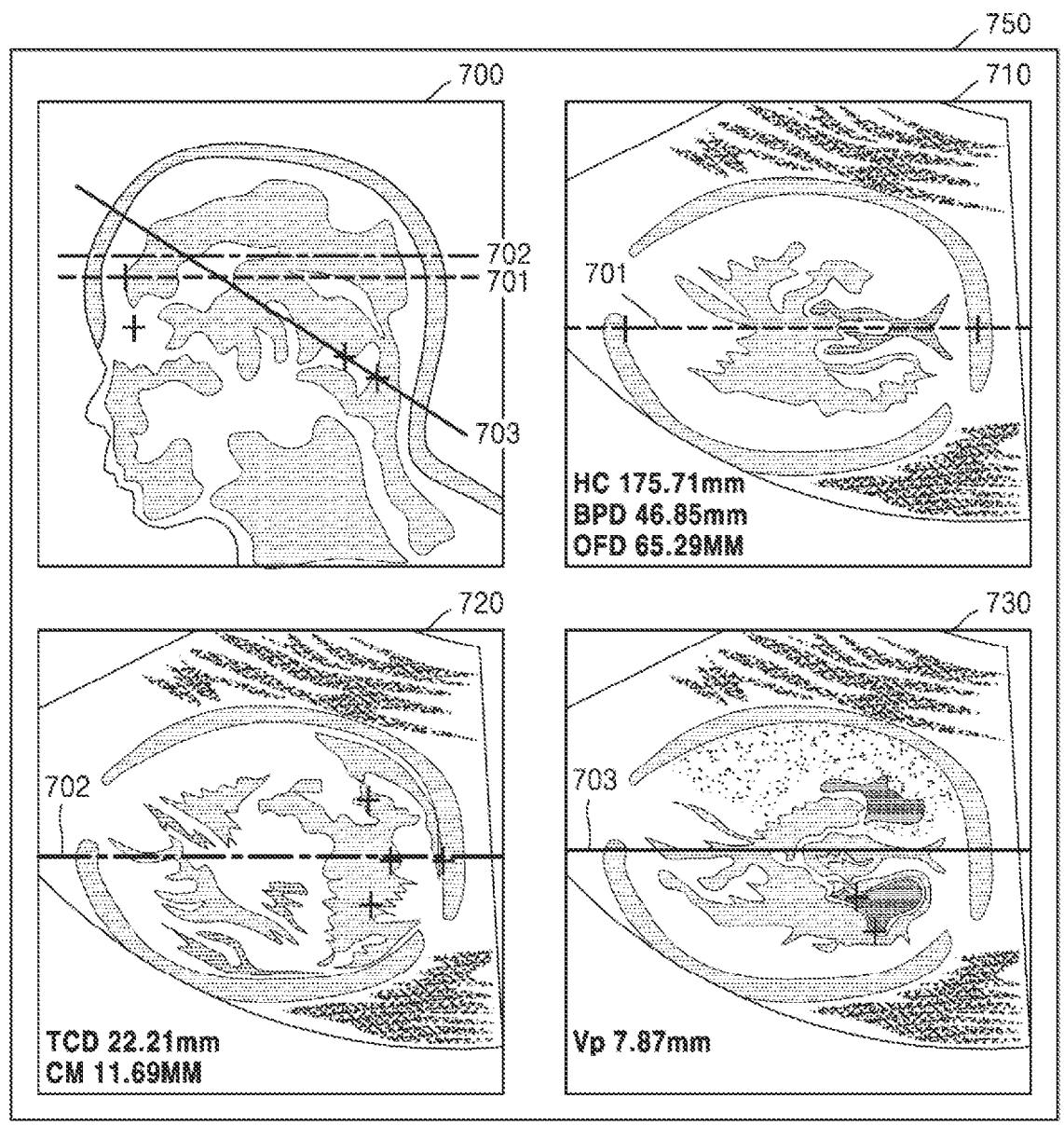
FIG. 7 is an exemplary diagram of a screen according to an exemplary embodiment.

FIG. 7 is an exemplary diagram of a screen 750 according to an exemplary embodiment.

Referring to FIG. 7, the screen 750 displayed on the display 530 may include a plurality of ultrasound images arranged in a predetermined layout.

In detail, the screen 750 shows a MSP image 700, a TTP image 710, a TCP image 720, and a TVP image 730. A plurality of lines 701 through 703 on the MSP image 700 respectively correspond to the TTP image 710, the TCP image 720, and the TVP image 730.

As described above, an ultrasound diagnosis apparatus according to exemplary embodiments may display an MSP and measurement planes on a single screen and indicate a correlation therebetween, e.g., by displaying the measurement planes as corresponding lines on the MSP, thereby allowing the user to visually determine whether a detected measurement plane is appropriate.

For example, the image processor 520 may indicate a position of at least one measurement plane on an MSP image. In other words, the position of the at least one measurement plane may be indicated on the MSP image by a line or color. Referring to FIG. 7, the plurality of lines 701 through 703 or color may accurately indicate which positions of the MSP image 700 respectively correspond to measurement planes 710 through 730.

In this case, the plurality of lines 701 through 703 may be indicated in different colors. Furthermore, the plurality of lines 701 through 730 may be indicated in the same colors as contours corresponding to the measurement plane images respectively, i.e., the TTP image 710, the TCP image 720, and the TVP image 730.

Furthermore, the image processor 520 may display a name of a measurement plane indicated on a measurement plane image in the same color as a line corresponding to the measurement plane on an MSP image.

In addition, positions of biometric parameters may be displayed in the MSP and measurement planes, as described in detail with reference to FIG. 8.

Figure 8:
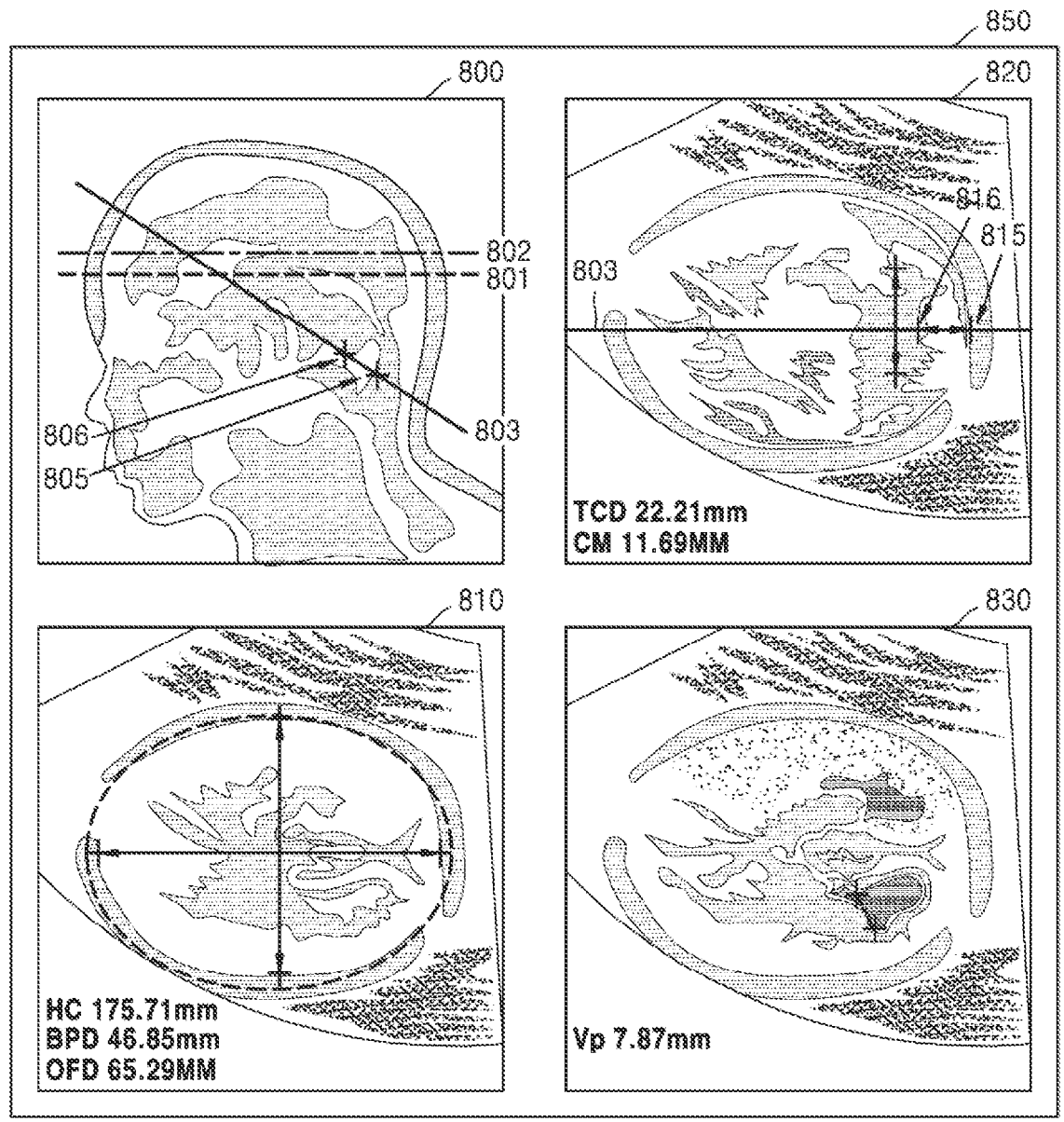
FIG. 8 is an exemplary diagram of a screen according to another exemplary embodiment.

FIG. 8 is an exemplary diagram of a screen 850 according to exemplary embodiments.

Referring to FIG. 8, the screen 850 shows a MSP image 800, a TTP image 810, a TCP image 820, and a TVP image 830.

A line 803 on the MSP image 800 corresponds to a line 803 on the TCP image 820. Two points 805 and 806 on the MSP image 800 respectively correspond to two points 815 and 816 on the TCP image 820. In this case, points included in a measurement plane image may be points corresponding to a biometric parameter. For example, a length of a straight line connecting the two points 815 and 816 may be a CM.

Furthermore, lines 801 and 802 on the MSP image 800 respectively correspond to the TTP image 810 and the TVP image 830.

According to exemplary embodiments, the line 803 and its corresponding line 803 and the points 805 and 806 and their corresponding points 815 and 816 indicated on the MSP image 800 and the TCP image 820 allow the user to accurately determine a relative position between an MSP and a measurement plane. Furthermore, the user may accurately identify a position of a biometric parameter on an MSP and a measurement plane.

Figure 9:
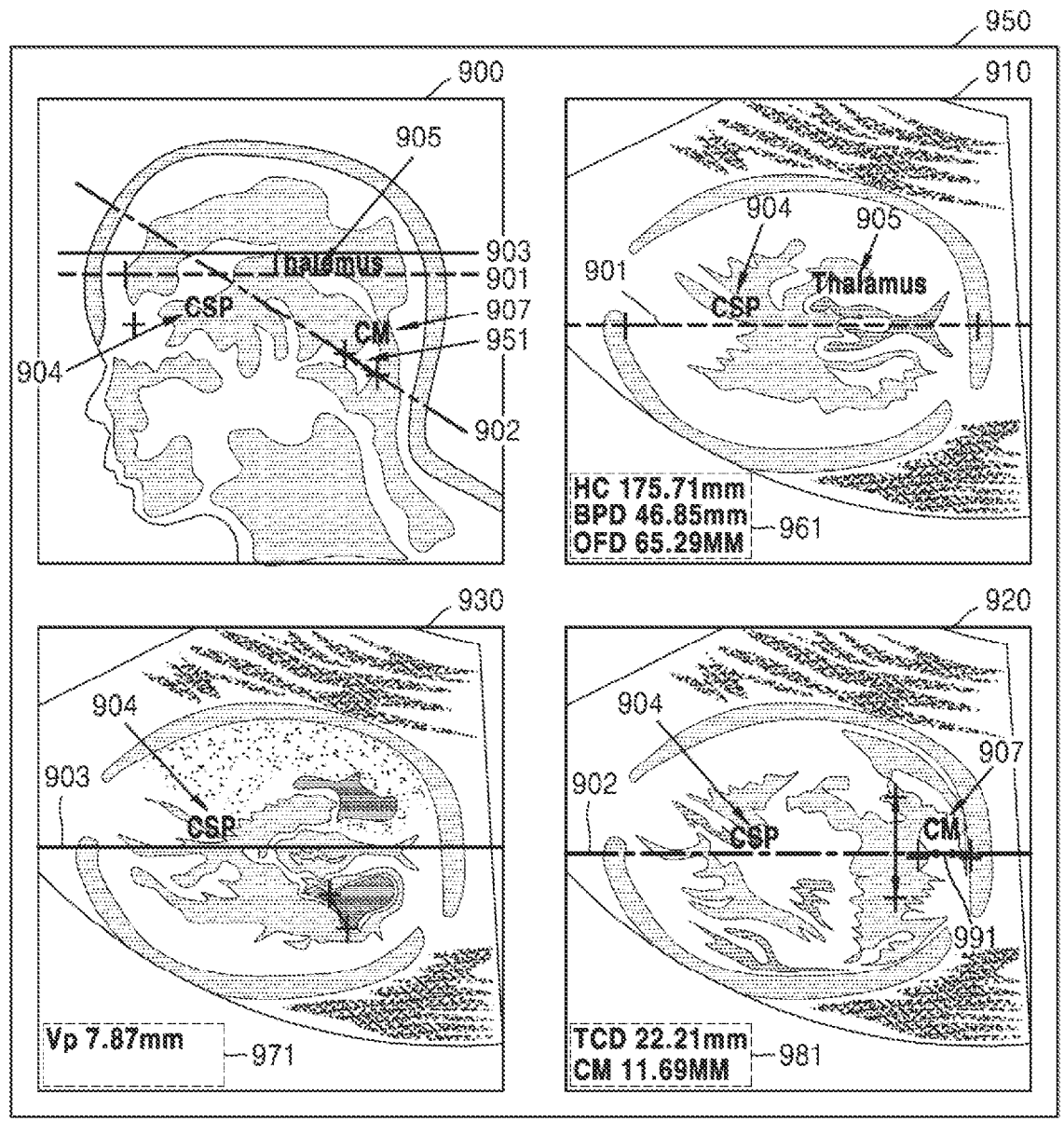
FIG. 9 is an exemplary diagram of a screen according to another exemplary embodiment.

FIG. 9 is an exemplary diagram of a screen 950 according to another exemplary embodiment.

Referring to FIG. 9, the screen 950 shows a MSP image 900, a TTP image 910, a TCP image 920, and a TVP image 930.

A plurality of lines 901 through 903 on the MSP image 900 respectively correspond to the TTP image 910, the TCP image 920, and the TVP image 930.

As seen on FIG. 9, a CSP line 904, a thalamus line 905, and CM 907 indicated on the MSP image 900 respectively correspond to CSP 904, Thalamus 905, and CM 907 on the TTP image 910, the TCP image 920, and the TVP image 930. In this way, an ultrasound diagnosis apparatus according to exemplary embodiments may visually indicate positions of biometric parameters on measurement planes as well as on an MSP.

Furthermore, a measured value may be indicated in an image corresponding to each measurement plane. For example, measured values 961 of HC, BPD, and OFD may be indicated in the TTP image 910. A measured value 971 of Vp and measured values 981 of TCD and CM may be indicated respectively on the TVP and TCP images 930 and 920.

Such measured values may be indicated using at least one of marker and text. For example, positions of biometric parameters may be indicated in the measurement plane images 910, 920, and 930 by using a mark 951, and the measured values 961, 971, and 981 may be respectively displayed on or near the measurement plane images 910, 930, and 920 as texts, etc. In this case, a marker and a text corresponding to one biometric parameter may be indicated in a different color than that in which a marker and a text corresponding to another biometric parameter are indicated in order to distinguish the biometric parameters from each other. The marker may be indicated by a sign + as shown in FIG. 9, but is not limited thereto. The marker may be indicated by another sign or color.

As described above, according to the exemplary embodiments, the ultrasound diagnosis apparatus 400 (500) may display a line corresponding to a measurement plane on an MSP image, thereby allow the user to simultaneously identify a position of the measurement plane, a position of a biometric parameter, and a measured value. This may help the user to determine the reliability of a result obtained by using an automatic measurement function.

Figure 10:
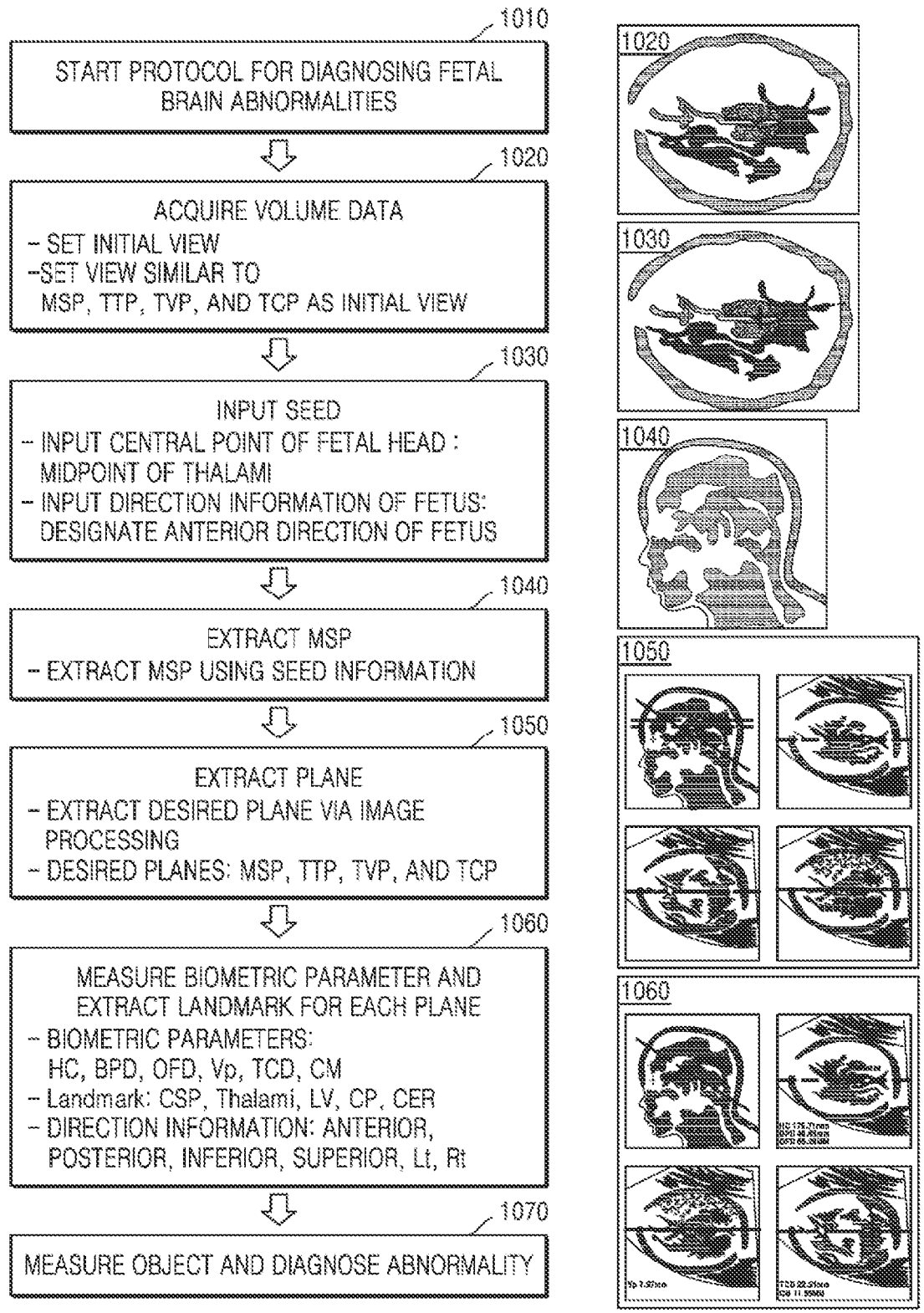
FIG. 10 is a diagram for explaining a protocol for diagnosing fetal brain abnormalities by using volume data, according to an exemplary embodiment.

FIG. 10 is a diagram for explaining a protocol for diagnosing fetal brain abnormalities by using volume data, according to exemplary embodiments.

The left side of FIG. 10 shows operations of the protocol according to the exemplary embodiments, and the right side shows screens, which are provided to a user, corresponding to the operations.

In operation 1020, the user sets an initial view (plane). In detail, the user may set an initial view that is similar to MPS, TTP, TVP, and TCP. The set initial view is displayed on a screen 1020 provided to the user.

In operation 1030, the user inputs a seed, and in particular, a central point of a fetal head and direction information of a fetus. In general, midpoints of thalami and an anterior direction of a fetus may respectively be designated as a central point of a fetal head and direction information of the fetus. A screen 1030, which is provided to the user, shows the central point of the fetal head and the direction information of the fetus which are indicated as a marker and a line, respectively.

In operation 1040, the ultrasound diagnosis apparatus 400 (500) extracts an MSP based on the seed input by the user. The extracted MSP is displayed on a screen 1040 provided to the user.

In operation 1050, the ultrasound diagnosis apparatus 400 performs image processing to extract TTP, TVP, and TCP. Since a process of extracting the measurement planes TTP, TVP, and TCP is described above with reference to FIG. 5, a detailed description thereof is omitted. The extracted MSP, TTP, TVP, and TCP are displayed on a screen 1050 having a 2×2 layout.

In operation 1060, the ultrasound diagnosis apparatus 400 may measure biometric parameters for each of the measurement planes TTP, TVP, and TCP as well as landmarks and direction information. Values of the biometric parameters, the landmarks, and the direction information may be indicated in the measurement planes TTP, TVP, and TCP and is then displayed on a screen 1060

In operation 1070, the user performs measurement of a fetal brain and diagnoses abnormality thereof based on the screens 1020, 1030, 1040, 1050, and 1060 on the right side of FIG. 10.

As described above, an ultrasound diagnosis apparatus 400 according to exemplary embodiments enables quicker and easier diagnosis of abnormality of a fetal brain based on volume data. Furthermore, the ultrasound diagnosis apparatus 400 allows the user to measure a desired position and check and modify the measured position. In addition, inter-observer variance and intra-observer variance in the measurement of a fetal brain may be reduced.

It will be understood by those of ordinary skill in the art that various changes in form and details may be made therein without departing from the spirit and scope of the inventive concept as defined by the following claims Thus, it should be understood that the exemplary embodiments described therein should be considered in a descriptive sense only and not for purposes of limitation. The scope of the inventive concept is defined not by the detailed description thereof but by the appended claims, and all differences within the scope of the appended claims and their equivalents will be construed as being included in the present inventive concept.

What is claimed is:

1. An ultrasound diagnosis apparatus comprising:
a display configured to display a mid-sagittal plane (MSP) image corresponding to the MSP of a head of an object; and
an image processor configured to determine at least one measurement plane based on the MSP, generate a measurement plane image corresponding to the at least one measurement plane, and indicate a position of the at least one measurement plane on the MSP,
wherein the display is further configured to display the at least one measurement plane image with the MSP image,
wherein the at least one measurement plane comprises at least one of a transthalamic plane (TTP), a transventricular plane (TVP), and a transcerebellar plane (TCP), and
wherein the image processor is further configured to determine the TTP based on the MSP, as a plane that is perpendicular to the MSP.

2. The ultrasound diagnosis apparatus of claim 1, wherein the image processor is further configured to detect the MSP from volume data for the head of the object and generate the MSP image.

3. The ultrasound diagnosis apparatus of claim 1, wherein the display is further configured to display a line, which indicates the position of the at least one measurement plane, on the MSP image.

4. The ultrasound diagnosis apparatus of claim 1, wherein the image processor is further configured to determine a plurality of measurement planes, generate a plurality of measurement plane images corresponding to the plurality of measurement planes, and indicate positions of the plurality of measurement planes on the MSP image by lines in a plurality of different colors, respectively.

5. The ultrasound diagnosis apparatus of claim 1, wherein the image processor is further configured to generate a TTP image corresponding to the TTP,
determine the TVP as a plane that is perpendicular to the MSP and horizontal to the TTP, generate a TVP image corresponding to the TVP,
determine the TCP by rotating the TTP around an axis extending through a cavum septi pellucidi (CSP) and generate a TCP image corresponding to the TCP.

6. The ultrasound diagnosis apparatus of claim 1, wherein the image processor is further configured to determine the measurement plane among a first plurality of candidate planes that are perpendicular to the MSP as the TPP, based on a brightness value of a first predetermined region of each of the first plurality of candidate planes, respectively.

7. The ultrasound diagnosis apparatus of claim 6, wherein the image processor is further configured to determine a second plurality of candidate planes that are perpendicular to the MSP and horizontal to the TTP, and determine one of the second plurality of candidate planes as the TVP based on a gradient magnitude of a second predetermined region of each of the second plurality of candidate planes, respectively.

8. The ultrasound diagnosis apparatus of claim 6, wherein the image processor is further configured to determine a cavum septi pellucidi (CSP) located at a predetermined distance from a central point of the head towards an anterior part of the head in the TTP, identify a third plurality of candidate planes by rotating the TTP around an axis extending through the CSP, and determine one of the third plurality of candidate planes as the TCP based on a similarity of a predetermined pattern in a third predetermined region of each of the third plurality of candidate planes, respectively.

9. The ultrasound diagnosis apparatus of claim 1, wherein the image processor is further configured to acquire a measured value by measuring at least one biometric parameter in the measurement plane image and indicate the measured value on the measurement plane image.

10. The ultrasound diagnosis apparatus of claim 9, wherein the image processor is further configured to indicate the measured value on the measurement plane image by using at least one from among a marker and a text.

11. The ultrasound diagnosis apparatus of claim 9, wherein the at least one biometric parameter comprises at least one from among a head circumference (HC), a biparietal diameter (BPD), an occipital frontal diameter (OFD), a transverse cerebellar diameter (TCD), a cisterna *magna* (CM), and a posterior ventricle (Vp).

12. The ultrasound diagnosis apparatus of claim 1, wherein the image processor is further configured to determine a plurality of measurement planes that are perpendicular to the MSP and generate a plurality of measurement plane images corresponding to the plurality of measurement planes,
the display is further configured to display the MSP image and the plurality of measurement plane images in a 2×2 layout.

13. A method of displaying an ultrasound image, the method comprising:
displaying a mid-sagittal plane (MSP) image corresponding to the MSP of a head of an object;
determining at least one measurement plane based on the MSP;
generating at least one measurement plane image corresponding to the at least one measurement plane;
indicating a position of the at least one measurement plane on the MSP;
displaying the at least one measurement plane image with the MSP image, wherein the at least one measurement plane comprises at least one of a transthalamic plane (TTP), a transventricular plane (TVP), and a transcerebellar plane (TCP), and wherein the determining the at least one measurement plane comprises: determining the TTP based on the MSP, as a plane that is perpendicular to the MSP.

14. The method of claim 13, further comprising:
detecting the MSP from volume data for the head of the object; and
generating the MSP image.

15. The method of claim 13, wherein the determining of the at least one measurement plane comprises determining a plurality of measurement planes which include the at least one measurement plane, the generating of the measurement plane image comprises generating a plurality of measurement plane images, which include the at least one measurement plane image, corresponding to the plurality of measurement planes, the displaying of the at least one measurement plane image comprises displaying the plurality of measurement plane images and a plurality of lines, which indicate positions of the plurality of measurement planes on the MSP image, in a plurality of different colors, respectively.

16. The method of claim 15, wherein
the determining of the plurality of measurement planes comprises:
determining the TVP as a plane that is perpendicular to the MSP and horizontal to the TTP; and
determining the TCP by rotating the TTP around an axis extending through a cavum septi pellucidi (CSP), and
the generating of the plurality of measurement plane images comprises:
generating a TTP image corresponding to the TTP;
generating a TVP image corresponding to the TVP; and
generating a TCP image corresponding to the TCP.

17. The method of claim 13, wherein the determining of the measurement plane comprises determining the measurement plane among a first plurality of candidate planes that are perpendicular to the MSP as the TTP, based on a brightness value of a first predetermined region of each of the first plurality of candidate planes, respectively.

18. The method of claim 17, further comprising:
determining a second plurality of candidate planes that are perpendicular to the MSP and horizontal to the TTP;
determining one of the second plurality of candidate planes as the TVP based on a gradient magnitude of a second predetermined region of each of the second plurality of candidate planes, respectively;
determining a cavum septi pellucidi (CSP) located at a predetermined distance from a central point of the head towards an anterior part of the head in the TTP;
identifying a third plurality of candidate planes by rotating the TTP around an axis extending through the CSP; and
determining one of the third plurality of candidate planes as a transcerebellar plane (TCP) based on a similarity of a predetermined pattern in a third predetermined region of each of the third plurality of candidate planes, respectively.

19. The method of claim 13, further comprising:
acquiring a measured value by measuring at least one biometric parameter in the measurement plane image; and
indicating the measured value on the measurement plane image by using at least one from among a marker and a text,
wherein the at least one biometric parameter comprises at least one from among a head circumference (HC), a biparietal diameter (BPD), an occipital frontal diameter (OFD), a transverse cerebellar diameter (TCD), a cisterna *magna* (CM), and a posterior ventricle (Vp).

20. A non-transitory computer-readable recording medium having stored therein a program for performing the method of claim 13.

* * * * *